United States Patent [19]

Iwayama et al.

[11] Patent Number: 5,180,862
[45] Date of Patent: Jan. 19, 1993

[54] PROCESS FOR ISOMERIZING TRICHLOROBENZENE

[75] Inventors: Kazuyoshi Iwayama; Hiroaki Honda, both of Aichi, Japan

[73] Assignee: Toray Industries, Inc., Japan

[21] Appl. No.: 753,929

[22] Filed: Sep. 3, 1991

[30] Foreign Application Priority Data

Sep. 3, 1990 [JP] Japan .................. 2-233550

[51] Int. Cl.$^5$ .................. C07C 25/10; C07C 17/00
[52] U.S. Cl. .................. 570/202; 570/190
[58] Field of Search .................. 570/202, 190

[56] References Cited

U.S. PATENT DOCUMENTS

| 4,409,407 | 10/1983 | Petruck et al. | 570/202 |
| 4,629,815 | 12/1986 | Soula | 570/202 |
| 4,806,697 | 2/1989 | Rule et al. | 570/202 |
| 4,806,698 | 2/1989 | Rule et al. | 570/202 |
| 4,935,561 | 6/1990 | Eichler et al. | 570/202 |
| 4,962,245 | 10/1990 | Kanai et al. | 570/202 |
| 5,043,493 | 8/1991 | Neuber et al. | 570/202 |

FOREIGN PATENT DOCUMENTS

| 0041850 | 12/1981 | European Pat. Off. | |
| 0111957 | 6/1984 | European Pat. Off. | |
| 0278729 | 8/1988 | European Pat. Off. | 570/202 |
| 947304 | 8/1956 | Fed. Rep. of Germany | 570/202 |
| 1092269 | 11/1960 | Fed. Rep. of Germany | |
| 0144330 | 8/1983 | Japan | 570/202 |
| 2258329 | 11/1987 | Japan | 570/202 |
| 351818 | 10/1972 | U.S.S.R. | 570/202 |

OTHER PUBLICATIONS

"Selectively Absorbing Black Aluminum Coating Deposited By Vacuum Evaporation" by Hu Xingfang et al, Thin Solid Films, vol. 149, No. 1, May 11, 1987, pp. 105-111. (p. 106, lines 18-29; pp. 108-109, conclusions).

Primary Examiner—Werren B. Lone
Attorney, Agent, or Firm—Austin R. Miller

[57] ABSTRACT

A process for isomerizing trichlorobenzene is disclosed. In the process of the present invention, a mixture of trichlorobenzene isomers containing 1,3,5-trichlorobenzene and/or 1,2,3-trichlorobenzene in small concentrations is contacted with a catalyst including acid type mordenite zeolite or acid type beta zeolite and a rhenium component and/or silver component in liquid phase in the presence of hydrogen, thereby increasing concentrations of 1,3,5-trichlorobenzene and/or 1,2,3-trichlorobenzene in said mixture.

16 Claims, 1 Drawing Sheet

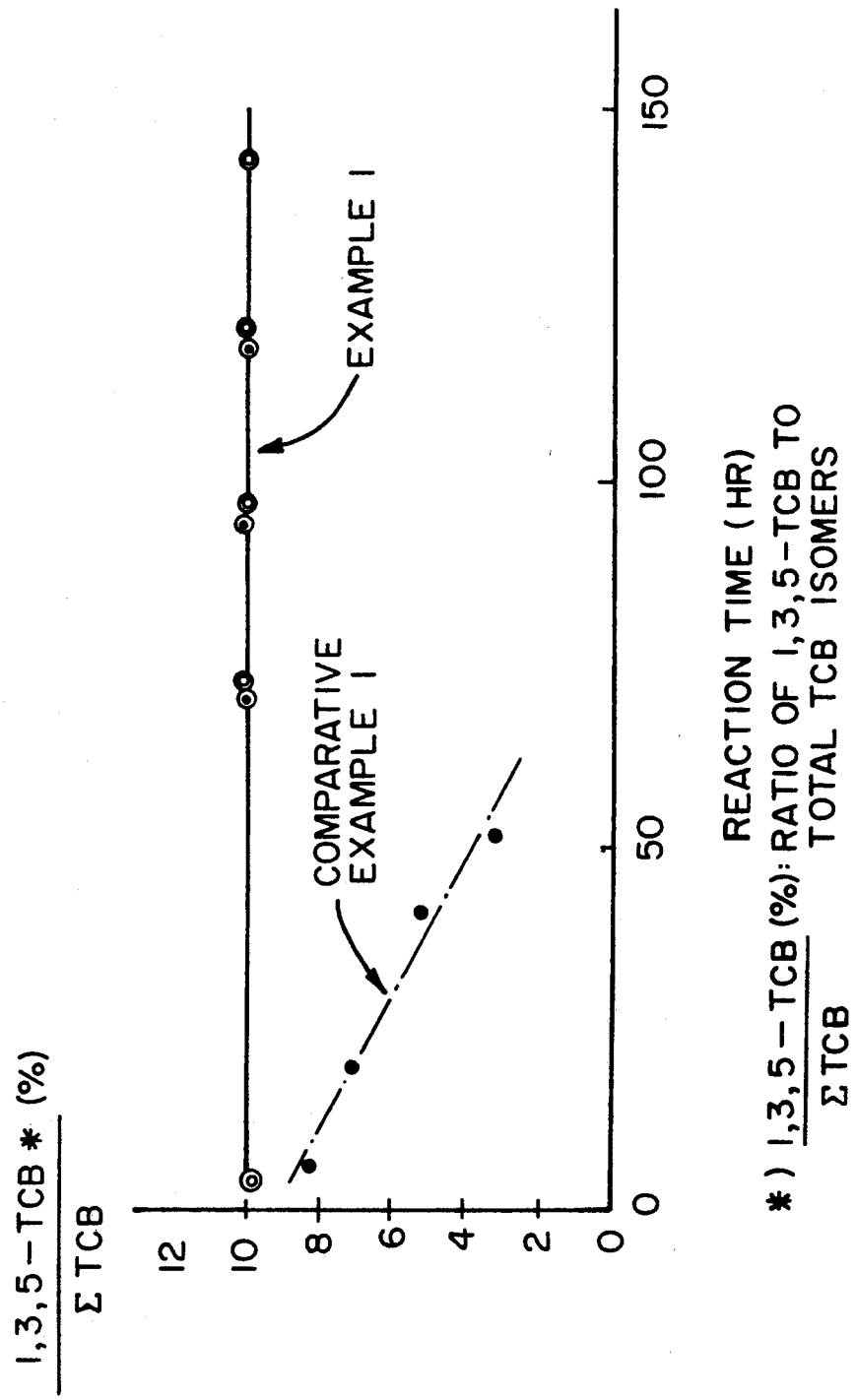

PROCESS FOR ISOMERIZING TRICHLOROBENZENE

BACKGROUND OF THE INVENTION

I. Field of the Invention

This invention relates to a process for isomerizing trichlorobenzene (hereinafter referred to as "TCB" for short). More particularly, this invention relates to a process for isomerizing TCB so as to produce 1,3,5-TCB and 1,2,3-TCB. 1,3,5-TCB and 1,2,3-TCB are useful as intermediates of pharmaceuticals and agricultural chemicals.

II. Description of the Related Art

TCB is usually produced by trichlorination of benzene. This reaction has a strong orientation so that most of the reaction product is 1,2,4-TCB. A typical reaction product of the trichlorination of benzene contains about 90% of 1,2,4-TCB, about 10% of 1,2,3-TCB and substantially no 1,3,5-TCB.

However, in equilibrated states, the concentration of 1,3,5-TCB is considerably high. G. H. Olah et al estimated the composition of the TCB isomers at 200° C. as follows (J. Org. Chem. 27, 3449 (1962)):

| | |
|---|---|
| 1,2,5-TCB | 65% |
| 1,2,3-TCB | 4% |
| 1,3,5-TCB | 31% |

Thus, judging from this composition in the equilibrated state, it is believed that 1,3,5-TCB can be produced by isomerizing TCB with an acid catalyst. However, the reactivity of chlorobenzene is sharply decreased as the number of substituted chlorine atom is increased so that TCB cannot be isomerized by using a usual acid catalyst.

As for 1,2,3-TCB which is also useful as an intermediate of pharmaceuticals and agricultural chemicals, although this compound is generated by the trichlorination of benzene as mentioned above, to promote the economical efficiency, it is necessary to convert 1,2,4-TCB to 1,2,3-TCB after recovering 1,2,3-TCB from the trichlorination product of benzene.

A conventional process for isomerizing TCB is known in which a mixture of TCB isomers is contacted with acid type mordenite zeolite or acid type ZSM-5 zeolite (Japanese Patent Publication (Kokoku) No. 1-9972).

However, with this conventional process, the isomerization activity of the catalyst is reduced with time. Maintaining the catalytic activity, that is, the fact that the lifetime of the catalyst is long is very important for industrial processes. Thus, the problem of the deactivation of the catalyst encountered in the conventional process must be overcome.

SUMMARY OF THE INVENTION

Accordingly, an object of the present invention is to provide a process for isomerizing TCB in which the isomerization activity of the catalyst is not substantially reduced for a long time.

The present inventors intensively studied to find that the deactivation of catalyst is caused by a high boiling compound generated by dechlorination reaction, and that the deactivation of the catalyst by the high boiling compound may be prevented by the existence of rhenium and/or silver in the catalyst and by carrying out the isomerization reaction in the presence of hydrogen in liquid phase, thereby completing the present invention.

That is, the present invention provides a process for isomerizing trichlorobenzene comprising contacting, in liquid phase, a mixture of trichlorobenzene isomers containing trichlorobenzene selected from the group consisting of 1,3,5-trichlorobenzene and 1,2,3-trichlorobenzene in small concentrations with a catalyst including acid type mordenite zeolite or acid type beta zeolite and a rhenium component and/or silver component in the presence of hydrogen so as to increase concentrations of 1,3,5-trichlorobenzene and/or 1,2,3-trichlorobenzene in said mixture.

By the present invention, a process for isomerizing TCB in which the isomerization activity of the catalyst is not substantially reduced for a long time was provided. Thus, by the process of the present invention, isomerization of TCB or production of 1,2,3-TCB and/or 1,3,5-TCB may be carried out for a long time without substantially decreasing the reaction rate. Thus, the present invention will make a great contribution to the industrial production of 1,2,3-TCB and 1,3,5-TCB, and in turn, to the field of pharmaceuticals and agricultural chemicals.

BRIEF DESCRIPTION OF THE DRAWING

FIG. 1 graphically shows the relationship between the reaction time and the concentration of 1,3,5-TCB among the total TCB isomers which was produced by a process of an example of the present invention or by a process of a comparative example.

DETAILED DESCRIPTION OF PREFERRED EMBODIMENTS

In the process of the present invention, a mixture of TCB isomers containing 1,3,5-TCB and/or 1,2,3-TCB in small concentrations is subjected to the isomerization process. The term "small concentration" herein means that the concentrations of 1,3,5-TCB and/or 1,2,3-TCB are smaller than that in the equilibrated state at a temperature at which the isomerization reaction is carried out. "Small concentration" means that the concentrations of 1,3,5-TCB and/or 1,2,3-TCB can be increased by the isomerization reaction. Subjecting a mixture containing no 1,3,5-TCB and/or no 1,2,3-TCB to the process is also within the scope of the present invention since upon starting the isomerization reaction, 1,3,5-TCB and 1,2,3-TCB are formed so that the mixture is converted to a mixture containing small concentrations of 1,3,5-TCB and 1,2,3-TCB. According to the same logic, a process wherein pure TCB isomer other than 1,3,5-TCB and 1,2,3-TCB, such as pure 1,2,4-TCB, is subjected to the isomerization process is also within the scope of the present invention. From a practical view point, the trichlorination reaction product of benzene is a typical example of the starting material of the process of the present invention.

The catalyst used in the process of the present invention is based on an acid type zeolite selected from the group consisting of mordenite zeolite and beta zeolite.

The beta zeolite per se as well as its production process is known. For example, a production process of beta zeolite is disclosed in U.S. Pat. No. 3,308,069. A typical way to identify beta zeolite is to check the X-ray diffraction pattern. The characteristic X-ray diffraction pattern of beta zeolite is shown in Table 1 below.

TABLE 1

| Interplanar Spacing d (Å) | Intensity |
|---|---|
| 11.7 ± 0.2 | M |
| 4.18 ± 0.08 | M |
| 3.98 ± 0.08 | VS |
| 3.53 ± 0.08 | W |
| 3.35 ± 0.08 | M |
| 3.32 ± 0.08 | M |
| 3.08 ± 0.08 | W |
| 2.69 ± 0.08 | W |

In Table 1, VS means very strong, M means medium and W means weak.

The mordenite zeolite per se as well as its production process is known. For example, production processes of mordenite zeolite are disclosed in Japanese Patent Publication (Kokoku) No. 47-46677 and Japanese Laid-open Patent Application (Kokai) No. 58-91032. A typical way to identify mordenite zeolite is to check the X-ray diffraction pattern. The characteristic X-ray diffraction pattern of mordenite zeolite is shown in Table 2 below.

TABLE 2

| Interplanar Spacing d (Å) | Intensity |
|---|---|
| 13.6 ± 0.2 | M |
| 10.2 ± 0.2 | W |
| 9.00 ± 0.2 | S |
| 6.56 ± 0.1 | S |
| 6.40 ± 0.1 | M |
| 6.05 ± 0.1 | W |
| 5.80 ± 0.1 | M |
| 4.52 ± 0.08 | M |
| 3.99 ± 0.08 | S |
| 3.83 ± 0.08 | W |
| 3.76 ± 0.08 | W |
| 3.53 ± 0.05 | W |
| 3.46 ± 0.05 | VS |
| 3.38 ± 0.05 | S |
| 3.28 ± 0.05 | W |
| 3.20 ± 0.05 | S |
| 3.15 ± 0.05 | W |
| 2.89 ± 0.05 | M |
| 2.51 ± 0.05 | W |

The beta zeolite or the mordenite zeolite employed in the process of the present invention is acid type. As is well-known, acid type zeolite is obtained by substituting cations in the zeolite with protons or dior more valent cations. The proton-substituted acid type zeolites are preferred because of their high catalytic activity.

The substitution of the cations in the zeolite with protons may be carried out by treating the zeolite with an aqueous solution containing an acid so as to directly ion-exchange the cations with protons or by firstly ion-exchanging the cations with ammonium ions and then calcining the resultant. Further, in cases where the zeolite intrinsically contains organic nitrogen-containing cations, the zeolite can be converted to acid type by calcining the zeolite so as to decompose the organic nitrogen-containing cations, thereby converting the cations to protons. It is also preferred to conduct the ion-exchange step mentioned above in the formation of the zeolite so as to substitute alkaline metal ions such as sodium ions in the zeolite with protons.

The catalyst employed in the process of the present invention contains a rhenium component and/or silver component. As for the rhenium, it may exist in the form of simple substance or in the form of compounds such as oxides, selenides and the like. In either case, the catalyst preferably contains about 0.01-1.0% by weight of rhenium in terms of rhenium element, more preferably about 0.05-0.5% by weight. The rhenium component may be directly carried by the entire zeolite or by a part of the zeolite. Alternatively, the rhenium component may be carried on a refractory oxide such as aluminum oxide and the refractory oxide carrying the rhenium component may co-exist with the zeolite. Still alternatively, the rhenium component in the form of simple substance or in the form of a compound such as oxide, sulfide, halide or the like may be physically mixed with the zeolite. A preferred method for preparing a catalyst carrying the rhenium component is to immerse the zeolite in an aqueous solution of a water-soluble rhenium compound such as perrhenic acid or ammonium perrhenate.

On the other hand, the silver may usually be introduced in the zeolite by treating the zeolite with aqueous silver nitrate solution so as to carry out ion-exchange between the cations in the zeolite and silver ions. Alternatively, a salt of silver such as silver halide may be mixed with zeolite powder so as to introduce silver in the catalyst. The catalyst may preferably contain the silver component in terms of silver element in the amount of about 0.5-15% by weight, more preferably about 2-10% by weight. Needless to say, the catalyst may contain both of the rhenium component and the silver component.

The catalyst may usually be used in molded form. Any conventional molding method such as rolling method, extrusion method, compression method or the like may be employed. In the molding process, if necessary, a binder such as alumina sol or clay may be employed. The above-described ion-exchange step and the step of incorporation of the rhenium component and/or the silver component may be carried out at any stage before or after the molding of the catalyst. The molded zeolite catalyst is usually calcined at a temperature of 300°-700° C. so as to activate the same.

The isomerization of TCB is carried out in the presence of hydrogen ($H_2$). The amount of the hydrogen to exist in the reaction system may preferably be not less than 0.01 mol, more preferably not less than 0.03 mol per one mole of the total TCB isomers supplied to the process.

The isomerization process of the present invention is carried out in liquid phase. By carrying out the process in liquid phase, the high boiling compounds which are thought to be the cause of the deactivation of the catalyst are more readily removed from the reaction system.

The process may be carried out by employing a fixed bed, moving bed or fluidized bed. Among these, in view of the ease of operation, a flow method employing a fixed bed is preferred.

The isomerization process of the present invention may usually be carried out at a temperature of 250°-500° C., preferably at 300°-450° C. The pressure is not restricted as long as the reaction system is kept in liquid form. The weight hourly space velocity (WHSV) in the isomerization process may preferably be 0.05-10 $Hr^{-1}$, more preferably 0.1-5 $Hr^{-1}$.

By the above-described process, the concentrations of 1,3,5-TCB and/or 1,2,3-TCB in the mixture of the TCB isomers are increased. The 1,3,5-TCB and 1,2,3-TCB may be separated from the reaction product by conventional methods such as crystallization, distillation or combination thereof. The separation may also be carried out by economical adsorption methods such as disclosed in, for example, Japanese Laid-open Patent Application (Kokai) No. 58-219131, by which 1,3,5-TCB and 1,2,3-TCB with high purity may be obtained efficiently.

The invention will now be described by way of examples thereof. It should be noted, however, the examples are presented for illustration purposes only and should not be interpreted in any restrictive way.

EXAMPLE 1

In 254.1 g of water, 96.2 g of 20% aqueous solution of tetraethylammonium hydroxide and 16.8 g of aqueous solution of sodium aluminate ($Al_2O_3$ content: 19.5%, $Na_2O$ content: 20.2%) were dissolved.

To this solution, 52.6 g of silicic acid was added and the resultant was stirred to obtain an aqueous slurry. The composition of the slurry was as follows in terms of molar ratio.

| | |
|---|---|
| $SiO_2/Al_2O_3$ | 25 |
| $RN^+/(RN^+ + Na^+)$ | 0.544 |
| (wherein R means organic groups) | |
| $OH^-/SiO_2$ | 0.30 |
| $H_2O/OH^-$ | 80 |

The slurry was fed in a 500 ml autoclave and after sealing, the temperature of the slurry was raised to 160° C. The reaction was carried out under stirring for 11 days. Thereafter, the reaction product was cooled, filtered and washed 5 times with water, followed by being dried overnight at about 120° C.

The obtained product was examined by the X-ray diffraction method. The resulted X-ray diffraction pattern is shown in Table 3 below. From this pattern, the product was identified as beta zeolite. The molar ratio of $SiO_2/Al_2O_3$ was 21.0.

TABLE 3

| Interplanar Spacing d (Å) | Intensity |
|---|---|
| 11.82 | 29 |
| 4.17 | 15 |
| 3.986 | 100 |
| 3.534 | 7 |
| 3.331 | 15 |
| 3.041 | 13 |
| 2.690 | 6 |

To the beta zeolite powder prepared as described above, alumina sol was added in the amount of 15% in terms of $Al_2O_3$ based on the weight of the zeolite. After kneading the mixture, the resultant was extruded from 14-24 mesh and then calcined at 500° C. for 2 hours in the air. The resulting molded beta zeolite was subjected to an ion-exchanging step 5 times with 10 wt % aqueous ammonium chloride solution at a solid-liquid ratio of 2 l/kg at 90° C., followed by being sufficiently washed with water. The resulting zeolite was then immersed for two hours in aqueous perrhenic acid solution containing 0.5% of rhenium in terms of rhenium element based on the weight of the catalyst. After draining the liquid, the resultant was dried overnight at 120° C., and then calcined at 540° C. for 2 hours. The thus obtained catalyst is hereinafter referred to as "Catalyst A". Using Catalyst A and a flow type fixed bed reactor, the isomerization of TCB was carried out in liquid phase in the presence of hydrogen under the following conditions, and the lifetime of the catalyst was examined.

| Reaction Conditions | |
|---|---|
| WHSV | $0.25\ Hr^{-1}$ |
| Reaction Temperature | 390° C. |
| Reaction Pressure | 40 $kg/cm^2$-G |
| $H_2$/Starting Material | 0.22 mol/mol |
| Starting Material | 100% 1,2,4-TCB |

The relationship between the reaction time and the concentration (%) of the generated 1,3,5-TCB is shown in FIG. 1.

COMPARATIVE EXAMPLE 1

A catalyst was prepared in the same manner as in Example 1 except that the treatment with the aqueous perrhenic acid solution was omitted, to obtain a catalyst containing no rhenium component. The obtained catalyst is hereinafter referred to as "Catalyst B".

The isomerization process was carried out in the same manner as in Example 1 except that Catalyst B was used in place of Catalyst A, and the lifetime of the catalyst was examined. The results are shown in FIG. 1.

As shown in FIG. 1, by comparing the results in Example 1 and Comparative Example 1, it can be seen that the reduction of the catalytic activity with time is much smaller in Catalyst A than Catalyst B, so that the lifetime of the catalyst is much improved by the existence of rhenium in the catalyst.

EXAMPLE 2

The same procedure as in Example 1 was repeated except that the aqueous perrhenic acid solution contained 0.2% of rhenium in terms of rhenium element based on the weight of the catalyst. The obtained catalyst is hereinafter referred to as "Catalyst C". Using Catalyst C, in liquid phase and in the presence of hydrogen, the isomerization of TCB was carried out under the conditions shown in Table 4 below. The results are also shown in Table 4.

As is apparent from Table 4, a part of 1,2,4-TCB was converted to 1,3,5-TCB and 1,2,3-TCB.

COMPARATIVE EXAMPLE 2

Using Catalyst C prepared in Example 2, the isomerization reaction was carried out in the absence of hydrogen under the conditions shown in Table 4. The results are shown in Table 4. It should be noted, however, since the reduction of the catalytic activity was too large, the data at 6 hours after the start of the reaction are shown. As can be seen from Table 4, in the absence of hydrogen in the reaction system, the recovery of the total TCB isomers is largely reduced. Further, the color of the reaction product was black. It is thought that a large amount of high boiling compounds are were generated to reduce the catalytic activity.

EXAMPLE 3

To the beta zeolite powder prepared in Example 1, alumina sol was added in the amount of 15% in terms of $Al_2O_3$ based on the weight of the zeolite. After kneading the mixture, the resultant was extruded from 14-24 mesh and then calcined at 500° C. for 2 hours in the air. The resulting molded beta zeolite was subjected to ion-exchanging step 5 times with 10 wt % aqueous ammonium chloride solution at a solid-liquid ratio of 2 l/kg at 90° C., followed by being sufficiently washed with water until the chloride ion did not exist in the zeolite.

Thereafter, the zeolite powder was immersed in aqueous silver nitrate solution containing 8% silver in terms of silver element based on the weight of the catalyst at a solid-liquid ratio of 3 l/kg at room temperature so as to carry out ion-exchange. The resulting zeolite was washed with water and dried overnight at 120° C., followed by being sintered at 540° C. for 2 hours. The thus obtained catalyst is hereinafter referred to as "Catalyst D".

Using Catalyst D, isomerization of TCB was carried out under the reaction conditions shown in Table 4 in liquid phase in the presence of hydrogen. The results are shown in Table 4.

EXAMPLE 4

To the beta zeolite powder prepared in Example 1, alumina sol was added in the amount of 15% in terms of $Al_2O_3$ based on the weight of the zeolite. After kneading the mixture, the resultant was extruded from 14-24 mesh and then calcined at 500° C. for 2 hours in the air. The resulting molded beta zeolite was subjected to an ion-exchanging step 5 times with 10 wt % aqueous ammonium chloride solution at a solid-liquid ratio of 2 l/kg at 90° C., followed by being sufficiently washed with water until the chloride ion did not exist in the zeolite.

Thereafter, the zeolite powder was immersed in aqueous silver nitrate solution containing 5% silver in terms of silver element based on the weight of the zeolite at a solid-liquid ratio of 3 l/kg at room temperature so as to carry out ion-exchange. The resulting zeolite was washed with water and was immersed in aqueous perrhenic acid solution containing 0.1% rhenium in terms of rhenium element based on the catalyst for 2 hours. After draining the liquid, the resulting zeolite was dried overnight at 120° C. and then calcined at 540° C. for 2 hours. The thus prepared catalyst is hereinafter referred to as "Catalyst E".

Using Catalyst E, isomerization of TCB was carried out under the reaction conditions shown in Table 4 in liquid phase in the presence of hydrogen. The results are shown in Table 4.

EXAMPLE 5

To mordenite zeolite powder with a silica/alumina molar ratio of 19.5, alumina sol was added in the amount of 15% in terms of $Al_2O_3$ based on the weight of the zeolite. After kneading the mixture, the resultant was extruded from 14-24 mesh and then calcined at 500° C. for 2 hours in the air. The resulting molded mordenite zeolite was subjected to an ion-exchanging step 5 times with 10 wt % aqueous ammonium chloride solution at a solid-liquid ratio of 2 l/kg at 90° C., followed by being sufficiently washed with water until the chloride ion did not exist in the zeolite.

Thereafter, the zeolite powder was immersed for two hours in aqueous perrhenic acid solution containing 0.5% rhenium in terms of rhenium element based on the weight of the catalyst. After draining the liquid, the resulting zeolite was dried overnight at 120° C., followed by being calcined at 540° C. for 2 hours. The thus obtained catalyst is hereinafter referred to as "Catalyst F".

Using Catalyst F, isomerization of TCB was carried out under the reaction conditions shown in Table 4 in liquid phase. The results are shown in Table 4.

EXAMPLES 6 AND 7

Using the same materials used in Example 1, a mixture slurry having the following composition was prepared:

| | |
|---|---|
| $SiO_2/Al_2O_3$ | 23.5 |
| $RN^+/(RN^+ + Na^+)$ | 0.528 |
| $OH^-/SiO_2$ | 0.32 |
| $H_2O/OH^-$ | 79 |

The slurry was fed in a 500 ml autoclave and after sealing, the slurry was aged at 60° C. for 24 hours. Then the temperature of the slurry was raised to 160° C. and the reaction was carried out under stirring for 10 days. Thereafter, the reaction product was cooled, filtered and washed 5 times with water, followed by being dried overnight at about 120° C.

The obtained product was examined by the X-ray diffraction method. The resulted X-ray diffraction pattern was substantially identical with that shown in Table 1. Thus, the product was identified as beta zeolite. The $SiO_2/Al_2O_3$ molar ratio of the product was 17.2.

To the beta zeolite powder thus prepared, alumina sol was added in the amount of 15% in terms of $Al_2O_3$ based on the weight of the zeolite. After kneading the mixture, the resultant was extruded from 14-24 mesh and then calcined at 500° C. for 2 hours in air. The resulting molded beta zeolite was subjected to an ion-exchanging step 5 times with 10 wt % aqueous ammonium chloride solution at a solid-liquid ratio of 2 l/kg at 90° C., followed by being sufficiently washed with water until the chloride ion did not exist in the zeolite.

Thereafter, the zeolite powder was immersed for two hours in aqueous perrhenic acid solution containing 0.5% rhenium in terms of rhenium element based on the weight of the catalyst. After draining the liquid, the resulting zeolite was dried overnight at 120° C., followed by being calcined at 540° C. for 2 hours. The thus obtained catalyst is hereinafter referred to as "Catalyst G".

Using Catalyst G, isomerization of TCB was carried out under the reaction conditions shown in Table 4 in liquid phase in the presence of hydrogen. The results are shown in Table 4.

TABLE 4

| | Example 2 | Comparative Example 2 | Example 3 | Example 4 | Example 5 | Example 6 | Example 7 |
|---|---|---|---|---|---|---|---|
| REACTION CONDITIONS | | | | | | | |
| WHSV ($Hr^{-1}$) | 0.25 | 0.25 | 0.25 | 0.25 | 0.25 | 0.60 | 0.25 |
| $H_2$/Fed TCB (mol/mol) | 0.22 | 0 | 0.22 | 0.22 | 0.11 | 0.22 | 0.22 |
| Reaction Temp. (°C.) | 390 | 390 | 390 | 390 | 390 | 390 | 390 |
| Reaction Pressure ($kg/cm^2$-G) | 40 | 40 | 40 | 40 | 40 | 40 | 40 |
| Reaction Time (Hr) | 144 | 6 | 124 | 140 | 124 | 120 | 144 |

TABLE 4-continued

|  | Example 2 | Comparative Example 2 | Example 3 | Example 4 | Example 5 | Example 6 | Example 7 |
|---|---|---|---|---|---|---|---|
| EXPERIMENTAL RESULTS | | | | | | | |
| LE (%) | 0.7 | 0.8 | 1.2 | 1.1 | 0.6 | 0.1 | 1.3 |
| CB (%) | 1.0 | 3.4 | 1.9 | 1.5 | 2.2 | 0.3 | 1.6 |
| DCB (%) | 9.6 | 24.6 | 14.8 | 12.7 | 16.5 | 4.7 | 12.4 |
| TCB (%) | 86.8 | 69.8 | 81.1 | 83.1 | 79.1 | 94.4 | 83.3 |
| TECB (%) | 1.3 | 0.3 | 0.8 | 1.1 | 1.2 | 0.3 | 1.1 |
| HE (%) | 0.5 | 1.1 | 0.3 | 0.5 | 0.5 | 0.2 | 0.3 |
| Recovery of TCB (%) | 86.8 | 69.8 | 81.1 | 83.1 | 79.1 | 94.4 | 83.3 |
| 1,3,5-TCB/ΣTCB | 10.5 | 7.9 | 10.7 | 10.9 | 7.5 | 9.2 | 16.5 |
| 1,2,3-TCB/ΣTCB | 10.1 | 9.8 | 9.8 | 9.6 | 10.3 | 10.7 | 9.4 |

Footnote:
Fed Materials: 1,2,4-TCB 100%
LE: Low Boiling Compounds, TECB: Tetrachlorobenzene, CB: Chlorobenzne, HE: High Boiling Compounds, DCB: Dichlorobenzene, ΣTCB: Total TCB Isomers Although the invention was described based on preferred examples thereof, it is apparent for those skilled in the art that various modifications may be made without departing from the spirit and scope of the present invention.

We claim:

1. A process for isomerizing trichlorobenzene comprising contacting, in liquid phase, a mixture of trichlorobenzene isomers containing trichlorobenzene selected from the group consisting of 1,3,5-trichlorobenzene and 1,2,3-trichlorobenzene in small concentrations with a catalyst selected from the group consisting of acid type mordenite zeolite and acid type beta zeolite, and a rhenium component and in the presence of hydrogen to increase concentrations of 1,3,5-trichlorobenzene and/or 1,2,3-trichlorobenzene in said mixture.

2. The process of claim 1, wherein said catalyst contains said rhenium component in a content of 0.01-1.0% in terms of rhenium element based on the weight of said catalyst.

3. The process of claim 1, wherein said hydrogen is present in an amount of not less than 0.01 mol per one mol of the total trichlorobenzene isomers supplied to the process.

4. The process of claim 1, wherein said isomerization is carried out at a temperature of 250°-500° C.

5. The process of claim 4, wherein said temperature is 300°-450° C.

6. The process of claim 1, wherein said isomerization is carried out at a weight hourly space velocity of 0.05-10 Hr$^{-1}$.

7. The process of claim 1, wherein said mixture of trichlorobenzene isomers is a product of trichlorination reaction of benzene.

8. A process for isomerizing trichlorobenzene comprising contacting, in liquid phase, a mixture of trichlorobenzene isomers containing trichlorobenzene selected from the group consisting of 1,3,5- trichlorobenzene and 1,2,3-trichlorobenzene in small concentrations with a catalyst selected from the group consisting of acid type mordenite zeolite and acid type beta zeolite, and a silver component in the presence of hydrogen to increase concentrations of 1,3,5-trichlorobenzene and/or 1,2,3-trichlorobenzene in said mixture.

9. The process of claim 8, wherein said catalyst contains said silver component in a content of 0.5-15% in terms of silver element based on the weight of said catalyst.

10. The process of claim 8, wherein said hydrogen is present in an amount of not less than 0.01 mol per one mol of the total trichlorobenzene isomers supplied to the process.

11. The process of claim 8, wherein said isomerization is carried out at a temperature of 250°-500° C.

12. The process of claim 11, wherein said temperature is 300°-450° C.

13. The process of claim 8, wherein said isomerization is carried out at a weight hourly space velocity of 0.05-10 Hr$^{-1}$.

14. The process of claim 8, wherein said mixture of trichlorobenzene isomers is a product of trichlorination reaction of benzene.

15. A process for isomerizing trichlorobenzene comprising contacting, in liquid phase, a mixture of trichlorobenzene isomers containing trichlorobenzene selected from the group consisting of 1,3,5-trichlorobenzene and 1,2,3-trichlorobenzene in small concentrations with a catalyst selected from the group consisting of acid type mordenite zeolite and acid type beta zeolite, and a rhenium component and a silver component in the presence of hydrogen to increase concentrations of 1,3,5-trichlorobenzene and/or 1,2,3-trichlorobenzene in said mixture.

16. The process of claim 15 wherein said catalyst contains said rhenium component in a content of 0.01-1.0% in terms of rhenium element based on the weight of said catalyst and said catalyst contains said silver component in a content of 0.5-15% in terms of silver element based on the weight of said catalyst.

* * * * *